United States Patent [19]

Clendinning et al.

[11] Patent Number: 4,716,211

[45] Date of Patent: Dec. 29, 1987

[54] SLURRY PROCESS FOR PRODUCING HIGH MOLECULAR WEIGHT CRYSTALLINE POLYARYLETHERKETONES

[75] Inventors: Robert A. Clendinning, New Providence; Louis M. Maresca, Belle Mead, both of N.J.

[73] Assignee: Amoco Corporation, Chicago, Ill.

[21] Appl. No.: 867,420

[22] Filed: May 15, 1986

Related U.S. Application Data

[63] Continuation of Ser. No. 710,119, Mar. 11, 1985, abandoned.

[51] Int. Cl.$^4$ .................. C08G 8/02; C08G 63/60; C08G 63/62

[52] U.S. Cl. .................. 528/126; 528/125; 528/128; 528/173; 528/174; 528/176; 528/179; 528/180; 528/181; 528/182; 528/193; 528/194

[58] Field of Search ............... 528/125, 126, 128, 173, 528/174, 176, 179, 180, 181, 182, 193, 194

[56] References Cited

U.S. PATENT DOCUMENTS

| | | | |
|---|---|---|---|
| 3,065,205 | 11/1962 | Bonner, Jr. ............ | 528/190 |
| 3,767,620 | 10/1973 | Angelo et al. ......... | 528/125 |
| 3,956,240 | 5/1976 | Dahl et al. ............ | 528/125 |

FOREIGN PATENT DOCUMENTS 0159826  9/1984  Japan .................. 528/176

*Primary Examiner*—Lucille M. Phynes
*Attorney, Agent, or Firm*—Donald M. Papuga; William H. Magidson; Ralph C. Medhurst

[57] ABSTRACT

Described herein is an improved process for preparing poly(aryl ether ketones) by reacting nucleophilic coreactants with electrophilic coreactants under Friedel Crafts polymerization conditions, wherein the improvement comprises carrying out the polymerization in a solvent comprising 1,2-dichlorethane.

8 Claims, No Drawings

SLURRY PROCESS FOR PRODUCING HIGH MOLECULAR WEIGHT CRYSTALLINE POLYARYLETHERKETONES

This application is a continuation of prior U.S. application Ser. No. 710,119 Filing Date 3/11/85 now abandoned.

TECHNICAL FIELD

This invention is directed to an improved process for preparing poly(aryl ether ketones) by reacting a nucleophilic coreactant with an electrophilic coreactant under Friedel-Crafts polymerization conditions, wherein the improvement comprises carrying out the polymerization in a solvent comprising 1,2-dichloroethane.

BACKGROUND OF THE INVENTION

The preparation of poly(ary ether ketones) by Friedel-Crafts polymerization techniques is well known in the art. For example, U.S. Pat. No. 3,065,205 describes the preparation of aromatic polyketones by Friedel-Crafts polymerization techniques using an organic solvent for the reaction. The solvents used are nitrobenzene, symmetrical tetrachloroethane, dichlorobenzene or carbon disulfide. Nitrobenzene is used as a solvent in all of the examples. The reaction mixture is stated as remaining homogeneous throughout the polymerization. However, the process described in U.S. Pat. No. 3,065,205 produces polymers of very low molecular weights and inherent viscosities ranging from 0.13 to 0.18, as measured in concentrated sulfuric acid.

In describing the difficulty in preparing polyketones such as those described in U.S. Pat. Nos. 3,065,205, 3,791,890 states the problem as the relatively intractable nature of the initial polymer-catalyst complex upon formation. The patent states the following in column 1, lines 10 to 20:

"Previous attempts to deal with the generally intractable state of the reaction product have included polymerizing the monomers in the presence of a soluble solid material to permit removing the product from the reaction medium and subsequently separating the soluble material by leaching. However, none of these prior techniques has proved entirely satisfactory."

In U.S. Pat. No. 3,791,890, an improved process is described in which polyketones are prepared in granular form in a two step process. In the first step diphenyl ether and at least one of terephthalic or isophthalic acid chlorides are reacted in the presence of o-dichlorobenzene, sym-tetrachloroethane, or dichloroethane as a solvent utilizing a Friedel-Crafts catalyst, such as aluminum chloride, at a temperature of from −15° C. to 0° C. All the examples use o-dichlorobenzene as the solvent. The patent states that an initial low reaction temperature is desirable to maintain control over the rate of reaction so that coagulation of the formed polyketone does not occur before dispersion can be effected. In the next step, the reaction mixture produced is dispersed into a fluid medium maintained at a temperature of at least 50° C. The fluid medium is described as any gas or liquid in which the polyketone formed is substatially unreactive at the temperature employed in the process. The dispersion into a heated fluid is stated to segregate the particles of polymer that are beginning to form in the initial reaction mixture and prevent the agglomeration of the particles into a gelatinous mass. A granular polyketone is thus recovered. However, in this patent no viscosities for the polyketone are reported.

In U.S. Pat. No. 3,668,057 describes the preparation of copolyketones with reduced viscositites of about 0.9 dl/g (as measured in concentrated sulfuric acid at 25° C.) under Freidel-Crafts polymerization conditions with o-dichlorobenzene as solvent. However, polymers with reduced viscosities of about 0.9 dl/g are boardline with regard to toughness in same end-use applications. Copolyketones with high reduced viscosities are possible using hydrofluoric acid as the solvent and boron trifluoride as the catalyst. However, due to the toxicity of hydrofluoric acid/boron trifluoride it is not a system which is conducive to commercialization.

THE INVENTION

In the present invention a one step process to prepare high molecular weight poly(aryl ether ketones) has been discovered. It has been found that the use of 1,2-dichloroethane as a solvent in Friedel-Crafts polymerization process produces poly(aryl ether ketones) of high molecular weight in comparison to processes where solvents such as nitrobenzene and o-dichlorobenzene are utilized. The process of this invention prepares higher molecular weight (reduced viscosity) poly(aryl ether ketones) directly without the need of the dispersion step as required in U.S. Pat. No. 3,791,890.

The poly(aryl ether ketones) prepared by the process of this invention have reduced viscosities ranging from about 0.1 dl/g to about 3.0 dl/g, preferably from about 0.5 dl/g to about 2.0 dl/g., as measured in concentrated sulfuric acid at 25° C. (concentration of 1 g/100 ml).

The poly(aryl ether ketones) may be prepared by reacting:
(a) a mixture of substantially equimolar amounts of
  (i) at least one electrophilic aromatic diacyl halide of the formula

  YOC—Ar—COY where —Ar— is a divalent aromatic radical such as phenylene, diphenylether-4,4'-diyl, diphenyl-4,4'-diyl, naphthalene-diyl, and the like, Y is halogen such as chlorine, bromine or iodine with chlorine being preferred, and COY is an aromatically bound acyl halide group, which diacyl halide is polymerizable with at least one aromatic compound of (a)(ii), and
  (ii) at least one aromatic nucleophilic compound of the formula

  H—Ar'—H where —Ar'— is a divalent aromatic radical such as diphenylether-4,4'-diyl, 2,7-dibenzofuranediyl, diphenyl-4,4'-diyl, diphenylmethane-4,4'-diyl, naphthalene-diyl, phenanthrenediyl, and the like, and H is an aromatically bound hydrogen atom, which compound is polymerizable with at least one diacyl halide of (a)(i), and
(b) at least one aromatic monoacyl halide of formula

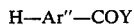
  H—Ar"—COY where —Ar"— is a divalent aromatic radical such as diphenylether-4,4'-diyl, diphenylmethane-4,4'-diyl, naphthalene-diyl, diphenyl-4,4'-diyl, 2,7-dibenzofuranediyl, and the like, and H is an aromatically bound hydrogen atom, Y is as defined above, and COY is an aromatically bound acyl halide group, which monoacyl halide is self-polymerizable, and (c) a combination of (a) and (b).

Specifically, the polyketones may be prepared by reacting one or more of the following nucleophilic coreactants: diphenyl sulfide, dibenzofuran, thianthrene, phenoxathin, phenodioxin, diphenylene, diphenyl, dibenzodioxine, xanthone, 4,4'-diphenoxybiphenyl, 2,2'-diphenoxybiphenyl, 1,2-diphenoxybenzene, 1,3-diphenoxybenzene, 1,4-diphenoxybenzene, 1-phenoxynaphthalene, 1,2-diphenoxynaphthalene, diphenyl ether, 1,5-diphenoxynaphthalene.

Similarly, the following electrophilic aromatic coreactant candidates for polyketone formation may be useful: terephthaloyl chloride, isophthaloyl chloride, thio-bis(4,4'-benzoyl chloride), benzophenone-4,4'-di(carbonyl chloride), oxy-bis(4,4'-benzoyl chloride), oxy-bis(3,3'-benzoyl chloride), diphenyl-3,3'-di(carbonyl chloride), carbonyl-bis(3,3'-benzoyl chloride), sulfonyl-bis(4,4'-benzoyl chloride), sulfonyl-bis(3,3'-benzoyl chloride), sulfonyl-bis(3,4'-benzoyl chloride), thio-bis(3,4'-benzoyl chloride), diphenyl-3,4'-di(carbonyl chloride), oxy-bis[4,4'-(2-chlorobenzoyl chloride)], naphthalene-1,6-di(carbonyl chloride), naphthalene-1,7-di(carbonyl chloride), naphthalene-1,5-di(carbonyl chloride), naphthalene-2,6-di(carbonyl chloride), oxy-bis[7,7'-naphthalene-2,2'-di(carbonyl chloride)], thio-bis[8,8'-naphthalene-2,2'-di(carbonyl chloride)], 7,7'-binaphthyl-2,2'-di(carbonyl chloride), diphenyl-4,4'-di(carbonyl chloride), carbonyl-bis[7,7'-naphthalene-2,2'-di(carbonyl chloride)], sulfonyl-bis[6,6'-naphthalene-2,2'-di(carbonyl chloride)], dibenzofuran-2,7-di(carbonyl chloride) and the like, or the combination of any of the above.

In addition to the electrophilic aromatic coreactants carbonyl chloride (phosgene), carbonyl dibromide, carbonyl difluoride or oxalyl chloride may be used.

Examples of compounds corresponding to the formula H—Ar"—COY include p-phenoxybenzoyl chloride, p-biphenyloxybenzoyl chloride, 4-(p-phenoxyphenyl) benzoyl chloride, 4-(p-phenoxybenzoyl) benzoyl chloride, 4(p-phenoxyphenoxy) benzoyl chloride 3-chlorocarbinyl dibenzofuran, 1-naphthoyl chloride, 2-naphthoyl chloride, and the like.

Preferably, diphenyl ether is reacted with terephthaloyl chloride and/or isophthaloyl chloride.

The preferred Friedel-Crafts catalysts are aluminum chloride, antimony pentachloride and ferric chloride. Other Friedel-Crafts catalysts, such as aluminum bromide, boron trifluoride, zinc chloride, antimony trichloride, ferric bromide and stannic chloride, can also be used.

The reaction may be carried out over a range of temperatures of from about 0° C. to about 160° C. In general, it is preferred to carry out the reaction at a temperature in the range of between 0° and 30° C. However, in some cases it is advantageous to carry out the reaction at temperatures above 30° C. or below 0° C. The reaction is generally carried out at ambient pressure. However, in some instances it may be advantageous to carry out the reaction at pressures greater than atmospheric or at subatmospheric pressures.

The reaction is carried out in a solvent system containing at least 50 percent by weight of 1,2-dichloroethane.

The reaction may be carried out in the presence of a capping agent as described in U.S. patent application Ser. No. (D-14604) filed on an even date as this application in the name of L. M. Maresca and titles, "A Method For Stabilizing Poly(Aryl Ether Ketones)", commonly assigned.

Said application is directed to a method of stabilizing poly(aryl ether ketones) by reacting nucleophilic coreactants with electrophilic coreactants under heterogeneous Friedel-Crafts polymerization conditions by adding a nucleophilic and/or electrophilic capping agent during polymerization.

The nucleophilic capping agents are of the general formula:

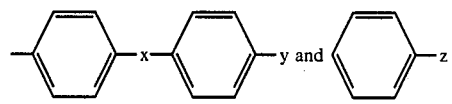

wherein x is a covalent bond, —O—, —S—, or —CR$_2$— wherein each R is independently hydrogen, an alkyl or fluoroalkyl group, preferably of 1 to 10 carbons, phenyl or an electron withdrawing group substituted phenyl. Preferably, x is a covalent bond, or O, y is NO$_2$,

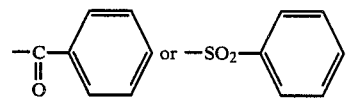

or if x is a covalent bond, y can also be hydrogen as well as any of the foregoing, z is halogen, alkyl or alkoxy Specific examples of appropriate nucleophilic capping agents are
4-nitrodiphenyl ether
4-phenoxybenzophenone
4-phenoxydiphenyl sulfone
anisole
fluorobenzene
chlorobenzene
biphenyl
toluene.
acetyl chloride The electrophilic capping agents correspond to the formula

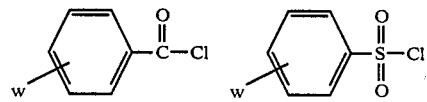

where w=halogen, alkyl, alkoxy, nitro,

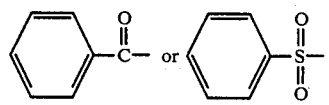

Specific examples of these end capping agents include the following
benzoyl chloride
p-fluorobenzoyl chloride
p-chlorobenzoyl chloride
p-methoxybenzoyl chloride
benzene sulfonyl chloride p-chlorobenzene sulfonyl chloride
p-methylbenzene sulfonyl chloride
4-benzoyl-benzoyl chloride The capping agents may be added anytime during or after the polymerization reaction but preferably are added with the reactants at the beginning of the polymerization reaction.

The polymer of this invention may include mineral fillers such as carbonates including chalk, calcite and dolomite; silicates including mica, talc, wollastonite; silicon dioxide; glass spheres' glass powders; aluminum; clay; quartz; and the like. Also, reinforcing fibers such as fiberglass, carbon fibers, and the like may be used. The polymers may also include additives such as titanium dioxide; thermal stabilizers, ultraviolet light stabilizers, plasticizers, and the like.

The polymers of this invention may be fabricated into any desired shape, i.e., moldings, coatings, films or fibers. They are particularly desirable for use as electrical insulation for electrical conductors.

EXAMPLES

The following examples serve to give specific illustrations of the practice of this invention but they are not intended in any way to limit the scope of this invention.

EXAMPLE 1

A 2 liter, 3 neck, round bottom flask was equipped with a mechanical stirrer, a nitrogen inlet, condenser and a thermometer. The flask was charged with 14.21 g (0.07 moles) of terephthaloyl chloride, 6.09 g (0.030 moles) of isophthaloyl chloride, 17.01 g (0.100 moles) of diphenyl ether and 700 mls of 1,2-dichloroethane. This solution was cooled to 5° C. in an ice water bath. Aluminum chloride (34.76 g, 0.260 moles) was added in portions while maintaining the temperature below 10° C. The resulting reaction mixture was held at 5°–10° C. for 6 hours. After ~30 minutes a precipitate formed. At the end of 6 hours the ice bath was removed and the reaction mixture was allowed to warm to ambient temperatures (~25° C.) where it was held for an additional 16 hours. The reaction mixture was poured into 3 liters of ice water containing 100 ml of concentrated hydrochloric acid. The resulting three phase system was heated to ~85° C. to distill the 1,2-dichloroethane. The polymer was isolated by filtration, washed with water (2×500 ml) and methanol (2×500 ml) and dried in a vacuum oven at 100° C. The product had a reduced viscosity of 1.62 dl/g as measured in concentrated sulfuric acid at 25° C. and a concentration of 1 g/100 ml.

Comparative Examples A–M

Example 1 was repeated using a variety of solvents, including those well known to be useful in Friedel-Crafts reactions. The results are summarized in Table 1.

TABLE 1

| Example | Solvent | Reduced Viscosity of Final Polymer (dl/g) |
| --- | --- | --- |
| A | Carbon Disulfide | 0.06 |
| B | 1,1,1-Trichloroethane | 0.07 |
| C | Methylene Chloride | 0.50 |
| D | Methylene Chloride | 0.92 |
| E | Carbon Tetrachloride | 0.07 |
| F | Trichloroethylene | 0.17 |
| G | Nitrobenzene | 0.18 |
| H | O—Dichlorobenzene | 0.31 |
| I | O—Dichlorobenzene[2] | 0.47 |
| J | O—Dichlorobenzene[3] | 0.51 |
| K | 1,2,4-Trichlorobenzene | 0.09 |
| L | Trichlorofluoromethane | 0.05 |
| M | 1,1,2-Trichlorotrifluoroethane | 0.04 |

[1]1% excess of diphenyl ether was used
[2]Four hours at 80° C. instead of 16 hours at 25° C.
[3]Six hours at 80° C. instead of 16 hours at 25° C.

Although relatively high molecular weight polymers can be prepared using methyl chloride, this solvent participates in the reaction resulting in alkylation of the polymer backbone as a major side product. Excess diphenyl ether is needed to obtain high molecular weight product because of this side reaction which consumes diphenyl ether and disrupts the reaction stoichiometry. These alkylated side products lead to polymer instability at elevated temperatures.

EXAMPLES 2–7

Example 1 was repeated except that a capping agent was added to control the molecular weight of polymer. The stoichiometry of the primary reactants is shown in the equation:

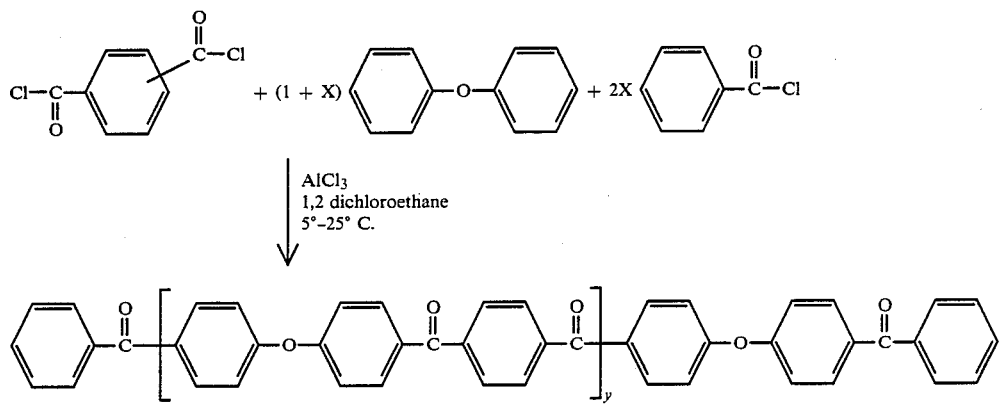

Reduced viscosity as a function of the end capping agent concentration is shown in Table 2.

TABLE 2

| Example | Terephthaloyl Chloride/ Isophthaloyl Chloride | X | Reduced Viscosity |
| --- | --- | --- | --- |
| 2 | 90/10 | .003 | 1.21 |
| 3 | 100/0 | .003 | 1.46 |
| 4 | 95/5 | .005 | .83 |

TABLE 2-continued

| Example | Terephthaloyl Chloride/ Isophthaloyl Chloride | X | Reduced Viscosity |
| --- | --- | --- | --- |
| 5 | 95/5 | .015 | .58 |
| 6 | 95/5 | .025 | .54 |
| 7 | 90/10 | .025 | .49 |
| 8 | 100/0 | .025 | .55 |
| 9 | 90/10 | .050 | .36 |
| 10 | 90/10 | .050 | .36 |
| 11 | 100/0 | .050 | .39 |
| 12 | 100/0 | .050 | .39 |

What is claimed is:

1. An improved process for preparing a poly(aryl ether ketone) by reacting nucleophilic coreactants with electrophilic coreactants under Friedel-Crafts polymerization conditions, wherein the improvement comprises carrying out the process in a solvent comprising 1,2-dichloroethane.

2. A process as defined in claim 1 wherein the poly(aryl ether ketone) is prepared by reacting one or more of the following nucleophilic coreactants: diphenyl sulfide, dibenzofuran, thianthrene, phenoxathin, phenodioxin, diphenylene, diphenyl, 4,4'-diphenoxybiphenyl, 2,2'-diphenoxylbiphenyl, 1,2-diphenoxybenzene, 1,3-diphenoxybenzene, 1,4-diphenoxybenzene, 1-phenoxynaphthalene, 1,2-diphenoxynaphthalene, diphenyl ether, or 1,5-diphenoxynaphthalene.

3. A process as defined in claim 1 wherein the poly(aryl ether ketone) is prepared by reacting one or more of the following electrophilic coreactants: phosgene, carbonyl difluoride, terephthaloyl chloride, isophthaloyl chloride, thio-bis(4,4'-benzoyl chloride), benzophenone-4,4'-di(carbonyl chloride), oxy-bis(4,4'-benzoyl chloride), oxy-bis(3,3'-benzoyl chloride), diphenyl-3,3'-di(carbonyl chloride), carbonyl-bis(3,3'-benzoyl chloride), sulfonyl-bis(4,4'-benzoyl chloride), sulfonyl-bis(3,3'-benzoyl chloride), sulfonyl-bis(3,4'-benzoyl chloride), thio-bis(3,4'-benzoyl chloride), diphenyl-3,4'-di(carbonyl chloride), diphenyl-4,4'-di(carbonyl chloride), oxy-bis[4,4'-(2-chlorobenzoyl chloride)], naphthalene-1,5-di(carbonyl chloride), naphthalene-1,6-di(carbonyl chloride), naphthalene-1,7-di(carbonyl chloride), naphthalene-2,6-di-(carbonyl chloride), oxy-bis[7,7'-naphthalene-2,2'-di(carbonyl chloride)], thio-bis[8,8'-naphthalene-2,2'-di(carbonyl chloride)], 7,7'-binaphthyl-2'-di(carbonyl chloride), carbonyl-bis[7,7'-naphthalene-2,2'-di(carbonyl chloride)], sulfonyl-bis[6,6'-naphthalene-2,2'-di(carbonyl chloride)], or dibenzofuran-2,7-di(carbonyl chloride).

4. A process defined in claim 1 wherein the reactant and/or correactant is selected from 4-phenoxybenzoyl chloride, 1-phenoxy-1-naphthalene carbonyl chloride, 4-phenoxy-4'-chlorocarbonyl diphenyl or 4-phenoxy-3'-chlorocarbonyl diphenyl ether.

5. A process as defined in claim 1 wherein diphenyl ether is reacted with terephthaloyl chloride and/or isophthaloyl chloride.

6. A process as defined in claim 1 wherein the process is carried out in the presence of a Freidel-Crafts catalyst selected from aluminum chloride, antimony pentachloride or ferric chloride.

7. A process as defined in claim 1 wherein the process is carried out at a temperature of from about 0° C. to about 25° C.

8. An improved process for preparing a poly(aryl ether ketone) by reacting diphenyl ether with terephthaloyl chloride and/or isophthaloyl chloride under Friedel-Crafts polymerization conditions, wherein the improvement comprises carrying out the process in a solvent comprising 1,2-dichloroethane.

* * * * *